United States Patent
Wolff (10) Patent No.: US 11,324,885 B2
(45) Date of Patent: May 10, 2022

(54) INFUSION DEVICE AND METHOD FOR ADMINISTERING A MEDICAL FLUID TO A PATIENT

(71) Applicant: Fresenius Vial SAS, Brézins (FR)

(72) Inventor: Rémy Wolff, Morette (FR)

(73) Assignee: Fresenius Vial SAS, Brézins (FR)

( * ) Notice: Subject to any disclaimer, the term of this patent is extended or adjusted under 35 U.S.C. 154(b) by 96 days.

(21) Appl. No.: 16/761,472

(22) PCT Filed: Oct. 16, 2018

(86) PCT No.: PCT/EP2018/078228
§ 371 (c)(1),
(2) Date: May 4, 2020

(87) PCT Pub. No.: WO2019/096518
PCT Pub. Date: May 23, 2019

(65) Prior Publication Data
US 2020/0289750 A1   Sep. 17, 2020

(30) Foreign Application Priority Data
Nov. 16, 2017 (EP) .................................. 17306589

(51) Int. Cl.
*A61M 5/168* (2006.01)
*A61M 5/142* (2006.01)

(52) U.S. Cl.
CPC ........ *A61M 5/16854* (2013.01); *A61M 5/142* (2013.01); *A61M 2005/16863* (2013.01);
(Continued)

(58) Field of Classification Search
CPC .... A61M 2005/16863; A61M 2205/18; A61M 2205/332; A61M 2205/3331;
(Continued)

(56) References Cited

U.S. PATENT DOCUMENTS

| 6,834,242 B2 | 12/2004 | Wolff et al. |
| 2016/0030668 A1* | 2/2016 | Barnes ................ A61M 5/00 604/67 |

FOREIGN PATENT DOCUMENTS

| CN | 1901953 A | 1/2007 |
| CN | 205041960 U | 2/2016 |

(Continued)

OTHER PUBLICATIONS

International Search Report and Written Opinion, counterpart International Appl. No. PCT/EP2018/078228, dated Jan. 14, 2019 (10 pages).

(Continued)

*Primary Examiner* — Jason E Flick
(74) *Attorney, Agent, or Firm* — Cook Alex Ltd.

(57) ABSTRACT

An infusion device (1) for administering a medical fluid to a patient (P) comprises a pump mechanism (11) for administering a medical fluid to a patient (P) through a line set (3), a sensor device (14) for measuring a measurement value indicative of a pressure in the line set (3), and a processor device (15) configured to automatically set, in an initial phase, a threshold value (15) to a value determined based on at least a mechanical characteristic of the line set (3) and/or the pump mechanism (11) and to determine, in an operational phase, whether an occlusion condition in the line set (3) is present based on the measurement value and the threshold value ($P_{thres}$) —Herein, the processor device (15) is configured to adjust the threshold value ($P_{thres}$) if in the operational phase a pressure variation condition in the line set (3) different than an occlusion condition is detected by the processor device (15). In this way an infusion device is provided which may be able to reliably detect an occlusion condition even in case of multiple infusion devices acting on a line set in a multiline infusion.

20 Claims, 3 Drawing Sheets

(52) U.S. Cl.
CPC ... *A61M 2205/18* (2013.01); *A61M 2205/332* (2013.01); *A61M 2205/3331* (2013.01); *A61M 2205/505* (2013.01); *A61M 2205/52* (2013.01); *A61M 2205/702* (2013.01)

(58) Field of Classification Search
CPC ........ A61M 2205/505; A61M 2205/52; A61M 2205/702; A61M 5/142; A61M 5/16854; A61M 5/14; A61M 5/168; A61M 5/16831; A61M 2205/33
See application file for complete search history.

(56) References Cited

FOREIGN PATENT DOCUMENTS

| EP | 1136089 | 9/2001 |
|---|---|---|
| EP | 2753378 A | 7/2014 |
| EP | 2902048 | 8/2015 |
| EP | 3167923 | 5/2017 |
| WO | WO97/07843 | 3/1997 |
| WO | WO2005/046768 | 5/2005 |
| WO | WO2014/059006 | 4/2014 |
| WO | WO2016/180011 | 11/2016 |
| WO | WO2017/032498 | 3/2017 |
| WO | WO2017/162447 | 9/2017 |

OTHER PUBLICATIONS

Office Action with English translation, counterpart Chinese App. No. 201880073799 (dated Nov. 26, 2021) (11 pages).

Search Report with English text, counterpart Chinese App. No. 201880073799 (dated Nov. 17, 2021) (2 pages).

* cited by examiner

INFUSION DEVICE AND METHOD FOR ADMINISTERING A MEDICAL FLUID TO A PATIENT

The present application is a U.S. National Stage of PCT International Patent Application No. PCT/EP2018/078228, filed Oct. 16, 2018, which claims priority to EP Application No. 17306589, filed Nov. 16, 2017, both of which are hereby incorporated herein by reference.

The invention relates to an infusion device for administering a medical fluid to a patient according to the preamble of claim 1 and to a method for controlling an infusion device for administering a medical fluid to a patient.

An infusion device of this kind comprises a pump mechanism for administering a medical fluid to a patient through a line set, a sensor device for measuring a measurement value indicative of a pressure in the line set, and a processor device configured to automatically set, in an initial phase, a threshold value to a value determined based on at least a mechanical characteristic of the line set and/or the pump mechanism and to determine, in an operational phase, whether an occlusion condition in the line set is present based on the measurement value and the threshold value.

An infusion device of this kind may generally be constituted for example by a syringe pump comprising a syringe to which the line set is connected and onto which a pumping mechanism in the shape of a pusher device acts in order to deliver a medical fluid from the syringe through the line set towards a patient. The infusion device however may also be constituted as a volumetric (peristaltic) infusion pump comprising a pumping mechanism, for example comprising a wobbling mechanism, acting onto the line set in order to pump medical fluid through the line set towards a patient.

Medication in a fluid state can be infused into a patient using a (disposable) line set. The line set is connected to a fluid source such as, in case of a syringe pump, a syringe that stores the medication. The medication can in this case be pushed out of the syringe through the line set towards the patient using a pusher device acting onto the syringe for continuously pushing a piston into a cylindrical tube in order to deliver medication from the cylindrical tube of the syringe via the line set towards the patient.

During such an infusion process an occlusion may occur in the line set, which, in some cases, may be hazardous for the patient. There hence is a need to reliably detect an occlusion occurring in a line set in order to avoid injuries resulting from occluded line sets.

From the state of the art methods for detecting an occlusion in a line set during an infusion process are known that are based on the assumption that an occlusion causes a rise of the pressure in the line set. An increase in pressure causes, in case of a syringe pump, the force applied to the syringe by a means of pumping device for pushing the medication through the line set towards the patient to increase. By monitoring the force applied to the syringe, hence, the actual pressure in the line set can be deduced and accordingly, if the actual pressure exceeds a threshold value, an alarm signal indicative of an occlusion can be triggered. In case of a volumetric (peristaltic) infusion device a force sensor may be placed directly on the line set in order to measure the pressure within the line set.

In this regard, WO2017/162447 A1 proposes to automatically set the threshold value based on a mechanical characteristic of the line set, such as a compliance of the line set. Taking the compliance of the line set into account and further based on a desired time which at maximum shall lapse between the actual occurrence of an occlusion in the line set and the moment at which the occlusion is detected by the processor device, the threshold value may be set to a value allowing for a fast detection of an occlusion.

Such automatic setting of the threshold works well, in particular in cases in which a single infusion device is acting on a single infusion line (i.e., the line set having a single line) for administering a medication to a patient. However, scenarios exist in which multiple infusion devices are connected via a line set comprising multiple infusion lines to a patient, such that multiple infusion devices act onto the line set and influence the pressure within the line set. In this case the occlusion detection at an infusion device based on the automatically set threshold value may potentially lead to false alarms, in particular in situations in which a bolus is injected by another infusion device into the line set, which may cause a pressure rise within the line set and may erroneously be identified as an occlusion condition by the infusion device.

For example, an infusion device in the shape of a syringe pump using for example a 50 mL syringe at a flow rate of 1 ml/h may automatically set its threshold to 50 mmHg. If another infusion device administers a bolus through the same line set, it in this case may occur that the pressure in the line set may rise beyond 50 mmHg due to the administration of the bolus, potentially leading to false alarms.

There hence is a desire to be able to differentiate an occlusion condition from another pressure variation condition in a line set which is not due to an occlusion.

In this regard, EP 1 136 089 B1 proposes to provide for a data communication in between multiple infusion devices in order to identify a potential source of a pressure variation in a line set.

It is an object of the instant invention to provide an infusion device and a method for controlling an infusion device which may be able to reliably detect an occlusion condition even in case of multiple infusion devices acting on a line set in a multiline infusion.

This object is achieved by means of an infusion device comprising the features of claim 1.

Accordingly, the processor device is configured to adjust the threshold value if in the operational phase a pressure variation condition in the line set different than an occlusion condition is detected by the processor device.

The infusion device hence, by means of its processor device, is configured to automatically set a threshold value for the occlusion detection. This takes place in an initial phase, based on a mechanical characteristics of the line set and/or the pump mechanism, such as a compliance of the line set or a stiffness of the pump mechanism and furthermore based for example on settings by a user, for example a flow rate setting.

The automatically set threshold value is used during the subsequent operational phase, i.e. during the actual operation of the infusion device for administering a medical fluid to a patient. If during the actual operation it is found that for example a pressure value in the line set as detected by the sensor device exceeds the threshold value, it generally is concluded for an occlusion and, accordingly, an alarm is triggered.

Herein, however, in order to avoid false alarms at an infusion device due to a pressure variation in the line set due to sources external to the infusion device, for example due to other infusion devices acting on the same line set in a multiline infusion, the processor device is configured to adjust the threshold value if a corresponding (abnormal) pressure variation condition different than an occlusion condition is detected. In this case the threshold value, which has automatically been set in the initial phase, is adapted, in particular increased, such that a wrong triggering of an alarm due to a detected occlusion condition is avoided.

In one embodiment, for detecting the pressure variation condition a slope value indicative of a slope of the pressure in the line set is determined based on measurement values obtained from the sensor device. This slope value may be compared to an expected slope value, and if it is found that the slope value deviates from the expected slope value by more than a predetermined margin, it is concluded that a pressure variation condition different than an occlusion condition is present.

The detection of the (abnormal) pressure variation condition hence is based on a comparison of the actual slope to an expected slope (that can be expected during the presence of an occlusion). If it is found that the actual slope is at least close to the expected slope, it is assumed that no other condition than an occlusion condition is present on the line set. If however the actual slope deviates substantially from the expected slope, it is concluded that a condition different from an occlusion condition is present, which in particular may be due to a source of pressure variation in the line set external to the infusion device.

This is based on the fact that for a particular system using for example a particular syringe in connection with a particular line set the pressure inside the line will, in case of an occlusion, rise at a specific slope determined by the characteristics of the infusion line and the system. Hence, by observing the slope it can be determined whether the slope of the pressure within the line set is close to the slope that is expected in case of an occlusion or not. Hence, by monitoring whether the slope of the pressure within the line set falls into a range around the expected slope, it in principle can be detected whether an occlusion (or a similar abnormal condition) is present or not. In the current context the comparison to the expected slope can be used for differentiating an occlusion condition from other pressure variation conditions, such that based on the comparison with the expected slope the automatically set threshold value for the occlusion detection may be adjusted.

The expected slope can be computed taking characteristics of the system into account. Characteristics can be stored for example in a storage device such as a database of the infusion device, such that the expected slope can be computed prior to the start of an infusion process when, in case of a syringe pump, a particular syringe in connection with a particular line set to be used for an infusion process is identified to the system by a user, for example a nurse.

The expected slope, in case of a syringe pump, is for example influenced by the compliance of the syringe, the compliance of the line set, a stiffness of a pusher device and/or a dimension of the syringe. The compliance herein indicates a measure for the expansibility of the system, for example the expansibility of the cylindrical tube of the syringe used on the infusion device or the expansibility of the line set connected to the cylindrical tube. Generally, the compliance indicates the change of volume for a change in pressure and accordingly is stated for example in ml/bar. With respect to for example the line set, the compliance indicates by what volume the line set expands if the pressure increases by a certain margin.

The compliance of a syringe, for example, is dependent on different physical characteristics of the syringe. Among such characteristics are for example the elasticity of the cylindrical housing and the rubber stopper elasticity, the rubber stopper elasticity likely having a stronger influence on the syringe compliance. For determining the compliance for a particular syringe, a calibration measurement can be performed in which all characteristics of the syringe that could influence it (cylindrical housing, stopper, piston stiffness etc.) are naturally taken into account.

For different syringes and different line sets, different characteristic values, for example compliance values, can be stored in the system, such that a particular set of values is chosen to compute the expected slope if a particular syringe in connection with a particular line set is to be used for an infusion process.

In case of an infusion device in the shape of a volumetric (peristaltic) infusion pump the expected slope may be estimated from the compliance of the line set alone.

In one embodiment, the processor device may conclude for a pressure variation condition different than an occlusion condition if the slope value exceeds the expected slope value times a first predetermined constant. The first predetermined constant may for example have a value from 1 to 10, for example 3. If the slope value is larger than the constant times the expected slope, it hence is concluded for a variation condition different than an occlusion condition, due to for example a source of pressure variation in the line set external to the infusion device.

In other words, if the detected slope is found to be substantially larger than the expected slope, it is concluded that the rise in the pressure in the line set is not due to an occlusion, but due to another pressure source. In this case the processor device of the infusion device concludes that no occlusion is present, but another source acts on the line set, such as another infusion device, leading to a rise in the pressure in the line set. In this case, no occlusion alarm is raised by the infusion device, but the infusion device adjusts its threshold value, in particular by increasing the threshold value, such that no (false) alarm is triggered.

For example, the threshold value may be set to the maximum allowable threshold value defined in the system in case a pressure variation condition other than an occlusion condition is detected as described above. Alternatively, the threshold value may be set to the actual, measured pressure plus a predefined margin ($\Delta_{pressure}$), for example having a value of 50 mmHg.

For the further operation, then, the adjusted threshold value is used for the occlusion detection, i.e., an occlusion condition is identified only if the pressure in the line set as determined from measurement values of the sensor device exceeds the adjusted threshold value.

If during the further operation it is found that the (abnormal) pressure variation condition has ceased and no abnormal pressure rise in the line set due to an external pressure source is present any longer, the threshold value, in one embodiment, beneficially is reset to the original value that has been set during the initial phase. For example, if the slope value is detected to fall below a value corresponding to the expected slope value times a second predetermined constant and if for example furthermore it is found that the actual pressure in the line set has dropped below an initial value, it can be concluded that the (abnormal) pressure variation condition is no longer present, and the threshold value is reset to the original value that automatically has been determined during the initial phase.

The second predetermined constant may lie in the range between 0.5 and 10. The second predetermined constant may be different than the first predetermined constant, but may also have the same value.

For determining the threshold value during the initial phase, the processor device, in one embodiment, is configured to determine a first threshold value candidate based on a desired time between the time of an occurrence of an occlusion in the line set and the time of detecting the occlusion condition by the processor device. The threshold value determined in this way in particular may provide for a fast occlusion detection. The desired time indicates the time which lapses between the actual occurrence of the occlusion and the triggering of an alarm. The desired time may be programmed by a user, for example a nurse, when configuring the infusion device for performing an infusion operation. The desired time may, however, also be pre-programmed such that a default value for the desired time for example a time between 1 and 10 minutes, for example 2 minutes, is used as the desired time unless a user programs another value for the desired time.

By computing the first threshold value candidate using the desired time a (low) candidate value for the pressure threshold is obtained which may provide for a fast occlusion detection. The infusion device may store a compliance value associated with the syringe and/or the line set connected to the tube of the syringe. The processor device herein is constituted to compute the first threshold value candidate from a stored compliance value, a set flow rate and the desired time. In particular, the processor device may be constituted to compute the first threshold value candidate according to the following equation:

$$P_{thres,1}[\text{bar}] = \frac{T_{desired}[h] \cdot f[\text{ml}/h]}{C[\text{ml}/\text{bar}]}$$

Herein, $P_{thres,1}$ represents the first threshold value candidate (in bar), $T_{desired}$ represents the desired time (in hours) between the time of an occurrence of an occlusion in the line set and the time at which the pressure value exceeds the threshold value, C represents the compliance value (in ml/bar), and f represents the flow rate (in ml/h).

In one aspect, the storage device may store a multiplicity of compliance values associated with a multiplicity of different syringes and/or line sets. This is based on the finding that different syringes and different line sets generally have different compliances, depending on the structural built of the syringe and the line set and the materials used, for example. By storing different compliance values for different syringes and different line sets, when using a particular syringe and a particular line set the associated compliance value may be chosen and the first threshold value candidate may be determined accordingly.

In case of a syringe infusion pump, the first threshold value candidate computed from the desired time, according to another aspect, is not set per se as threshold value when determining the threshold value in the initial phase, but a second threshold value candidate is additionally computed and taken into account as a second criteria, this second criteria being chosen such that the likelihood for false alarms is kept small. Hence, the second criteria is chosen such that the setting of too low a pressure threshold is avoided, at the expense of a (slightly) longer time which may lapse between the actual occurrence of the occlusion and the triggering of an alarm (when the pressure exceeds the threshold value).

In one embodiment, an infusion device in the shape of a syringe pump comprises a receptacle for receiving a syringe having a tube containing a medical fluid and a piston movable with respect to the tube, and a pusher device for acting onto the piston for pumping the medical fluid from the tube towards a patient. The second threshold value candidate, in one embodiment, is computed based on a force error estimate of a possible deviation between an expected frictional force and a true frictional force occurring when moving the piston relative to the tube.

Generally, the pressure value indicative of the pressure in the line set may for example be determined according to the following equation:

$$P = \frac{F - F_0}{S}.$$

Herein, P represents the pressure, F represents the measured force and $F_0$ represents a frictional force component. S represents the effective cross sectional surface of the tube (defined by its diameter). The measured force F is known from the sensor reading measuring the force in between the pusher device and the piston of the syringe. Also, the effective surface S is known from the geometry of the syringe used. However, the frictional force component $F_0$ generally may differ between different syringes of different types, models and volumes and even between different syringes of the same type, model and the volume. Generally, to derive the pressure value P, the frictional force component may be estimated, for example from a statistical analysis of different syringes of different types, models and volumes prior to conducting an actual infusion operation (this for example may be done by the manufacturer of the infusion device). Also, it is possible to model the behavior of the frictional force for different syringes of different types, models and volumes.

When computing the pressure value for detecting an occlusion, the frictional force component hence is estimated and is taken into account for deriving the pressure value. If no occlusion is present in the line set, it can be assumed that the pressure within the line set is (almost) 0, such that the frictional force component is comparable to the measured force. If there is an occlusion in the line set, however, the measured force will rise, and likewise the pressure value will rise. Hence, if during the operational phase the pressure value exceeds the set threshold value, it is concluded that an occlusion may be present and an alarm is triggered.

Because the frictional force component is subject to uncertainty and may differ between different syringes of different types, models and volumes and even between different syringes of the same type, model and volume, there may be a deviation between an expected frictional force (determined for example from statistical analysis by measuring the frictional behavior of different syringes) and the true frictional force occurring for the particular syringe used for the infusion. Because of this deviation, the pressure value derived from the above equation may not be fully accurate, such that the occlusion detection performed by comparing the derived pressure value with the threshold value may not be fully precise and in particular may cause false alarms if the actual frictional force occurring when moving the piston relative to the tube is for example smaller than the expected frictional force.

Hence, within the second criteria used to determine the threshold value a possible deviation between the true frictional force occurring when moving the piston relative to the tube and an expected frictional force is taken into account, this possible deviation being expressed as a force error estimate which indicates a possible deviating friction (as compared to an expected friction) when moving the piston relative to the tube.

For determining the second threshold value candidate, the storage device may store, for at least one particular syringe type, a mean frictional force required to move the piston relative to the tube and a standard deviation of the mean frictional force. The processor device, in this case, may be constituted to determine the force error estimate used to compute the second threshold value candidate using the standard deviation for a syringe of a particular syringe type, for example by multiplying the standard deviation by a constant factor. Hence, the storage device holds, for a particular syringe, a mean frictional force and a standard deviation for this mean frictional force. The mean frictional force is used to derive the pressure value for comparing it to the threshold value, as explained above. The standard deviation, in turn, is used to compute the force error estimate in order to obtain the second threshold value candidate, for example by multiplying the standard deviation by a constant factor, for example in the range between 1 and 4, for example 2.

The stored mean frictional force and/or the stored standard deviation may, in one aspect, be dependent on the position of the piston relative to the tube. This is based on the finding that the friction occurring between the piston and the tube may vary as the piston is moved within the tube. By storing position dependent mean frictional force values for a particular syringe and also position dependent standard deviation values for the particular syringe, hence, the frictional behavior may be modeled as a function of the position. In addition, the mean frictional force and/or the start standard deviation may vary as a function of the speed by which the piston is moved relative to the tube. Hence, the storage device may also hold different mean frictional force values and/or standard deviation values for different speeds of moving the piston relative to the tube.

The mean frictional force of a particular syringe may for example be obtained by measuring the frictional force when moving the piston relative to the tube in calibration tests prior to the actual infusion operation (such tests may for example be performed by the manufacturer of the device). The mean frictional force, and also the standard deviation, herein may be obtained by statistical analysis. As said, the mean frictional force and the standard deviation may be position dependent and also speed dependent.

Alternatively, the force error estimate may be determined from the mean frictional force alone stored in the storage device. For example, the force error estimate may be obtained by multiplying the mean frictional force by a constant factor, for example in the range between 1 and 3, for example 1.5. Again, the mean frictional force stored in the storage device may be dependent on the position of the piston relative to the tube and/or the speed by which the piston is moved relative to the tube.

In another alternative, the force error estimate may be stored directly as a parameter within the storage device. Hence, for different syringes of different types, different force error estimate parameters may be stored within the storage device.

The force error estimate indicates a possible deviation of a true frictional force from an expected frictional force (for example a mean frictional force stored in the system). The force error estimate hence indicates by what margin possibly the frictional force of an actually used syringe may differ from the frictional force component ($F_0$ in the equation above) used to derive the pressure value for comparing it to the threshold value. This force error estimate, as described above, may for example be derived from the standard deviation, or may be stored directly in the system. From the force error estimate, then, the second threshold value candidate may be computed according to the following equation:

$$P_{thres,2}[\text{bar}] = \frac{F_{est}[gf]}{10.2 \cdot S[\text{mm}^2]}$$

Herein, $P_{thres,2}$ represents the second threshold value candidate (in bar), $F_{est}$ represents the force error estimate (in gram force (gf)), and S represents the effective cross sectional surface (in mm$^2$) of the tube, defined as $S=\pi \cdot (D/2)^2$, D being the inner diameter of the cylindrical tube.

In one aspect, the threshold value in the initial phase may be set to be the maximum of the first threshold value candidate and the second threshold value candidate. Hence, the maximum of the two computed candidates is chosen as the threshold value, hence ensuring that a comparatively short time between the actual occurrence of the occlusion and the actual triggering of an alarm is obtained, but at the same time ensuring that the likelihood for false alarms is kept small.

The object is also achieved by a method for controlling an infusion device for administering a medical fluid to a patient, the method comprising:
  in an initial phase automatically setting, using a processor device of the infusion device, a threshold value to a value determined based on at least a mechanical characteristic of a line set and/or a pump mechanism for administering a medical fluid to a patient through the line set,
  in an operational phase determining, using the processor device, whether an occlusion condition in the line set is present based on a measurement value indicative of a pressure in the line set and the threshold value, and
  adjusting the threshold value if in the operational phase a pressure variation condition in the line set different than an occlusion condition is detected by the processor device.

The advantages and advantageous embodiments described above for the infusion device likewise apply also to the method, such that it shall be referred to the above.

The idea of the invention shall subsequently be described in more detail with reference to the embodiments shown in the figures. Herein.

Figure 1:
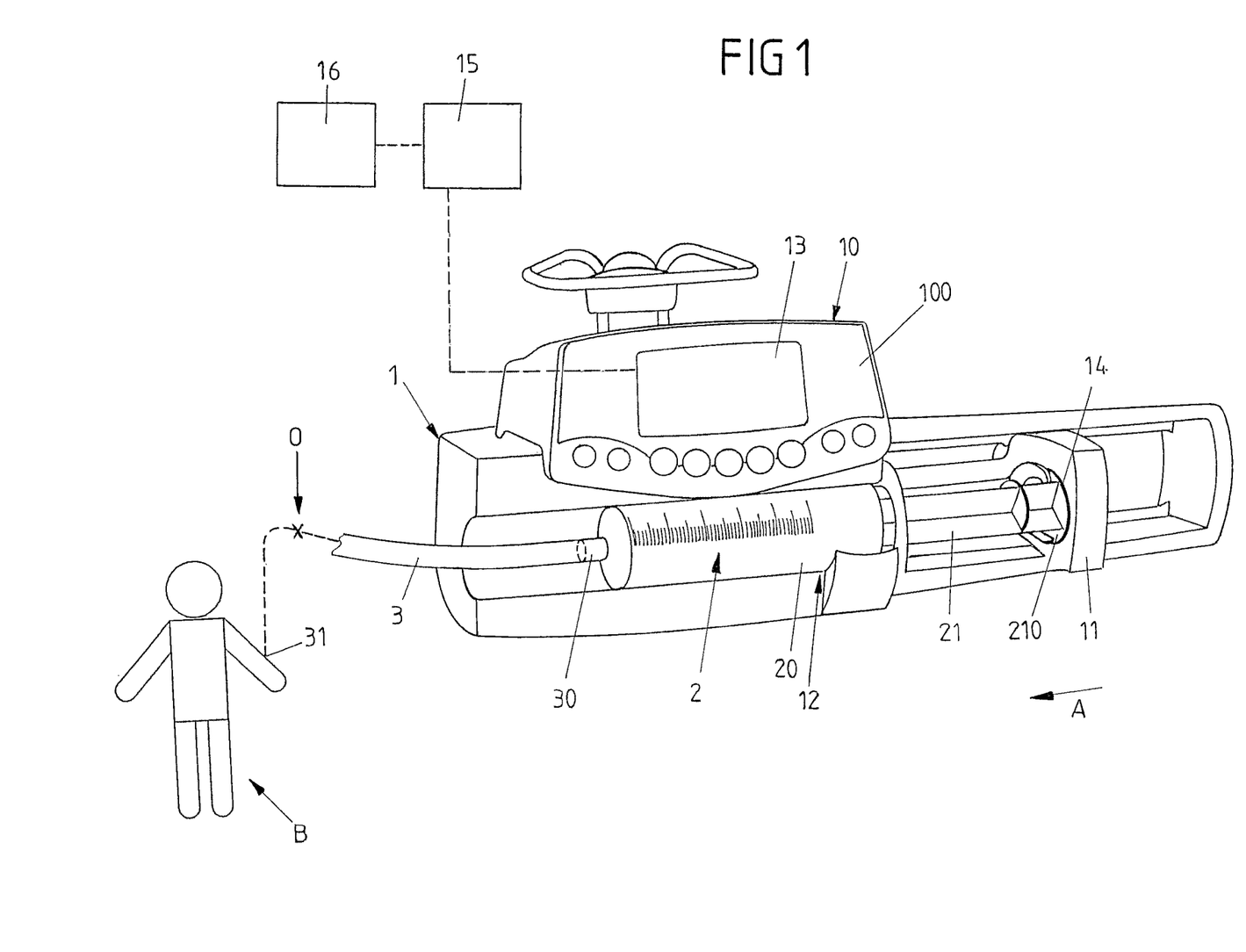
FIG. 1 shows a view of an infusion device constituted as a syringe pump.

FIG. 1 shows an embodiment of an infusion device 1 in the shape of a syringe pump. The infusion device 1 comprises a housing 10 having a front face 100 and a display device 13 arranged thereon. The display device 13 may for example be a touch-sensitive display allowing a user to enter commands for operation of the infusion device 1 and displaying operational information regarding the process of an actual infusion operation.

The infusion device 1 comprises a receptacle 12 in which a syringe 2 having a cylindrical tube 20 is arranged. A piston 21 is movable within the cylindrical tube 20 and is in engagement with a pusher device 11 of a pumping mechanism of the infusion device 1. At an end of the cylindrical tube 20 opposite the piston 21 a line set 3 extends from the cylindrical tube 20 towards a patient B, the line set 3 being connected to the cylindrical tube 20 at an end 30 and to the patient B at an end 31.

The piston 21 comprises a head 210 facing away from the cylindrical tube 20 and being in abutment with the pusher device 11 of the infusion device 1. During operation of the infusion device 1, the pusher device 11 is electromotorically driven in an actuation direction A such that the piston 21 is moved into the cylindrical tube 20 and a medical fluid contained in the cylindrical tube 20 is delivered via the line set 3 towards the patient B.

The infusion device 1 comprises a processor device 15 and a storage device 16. Via the processor device 15 the infusion operation of the infusion device 1 is controlled. In the storage device 16 operational parameters, such as mechanical characteristics of the syringe 2 used on the infusion device 1 as well as operational data, may be stored.

During an infusion process a medical fluid, for example a medication or a nutritional fluid for the parenteral feeding of a patient or the like, is delivered from the cylindrical tube 20 via the line set 3 towards the patient B. For this, the piston 21 is continuously pushed into the cylindrical tube 20 in an actuation direction A such that a desired flow rate is obtained, which is programmed by a user prior to the start of the infusion operation.

The line set 3 generally is made of a flexible tubing made for example from a PVC material. The line set 3 extends from the cylindrical tube 20 to the patient B and is, at its first end 30, in fluid connection with the cylindrical tube 20 and, at its second end 31, for example connected to a needle for providing an intravenous access to the patient B. During an infusion process an occlusion O in the line set 3 must be avoided and, if it nevertheless occurs, must be detected such that appropriate countermeasures to overcome the occlusion O can be taken. For this, a force sensor 14 is placed on the pusher device 11 facing the head 210 of the piston 21 for measuring a force exerted on the piston 21 during an infusion process. From a force measured by means of the force sensor 14 an estimate of the pressure within the syringe 2 can be obtained, such that the pressure within the syringe 2 and the line set 3 can be monitored. If it is found that the pressure within the syringe 2 and the line set 3 rises beyond a permissible threshold value, an alarm is triggered indicating that an occlusion O may be present in the system.

Figure 2:
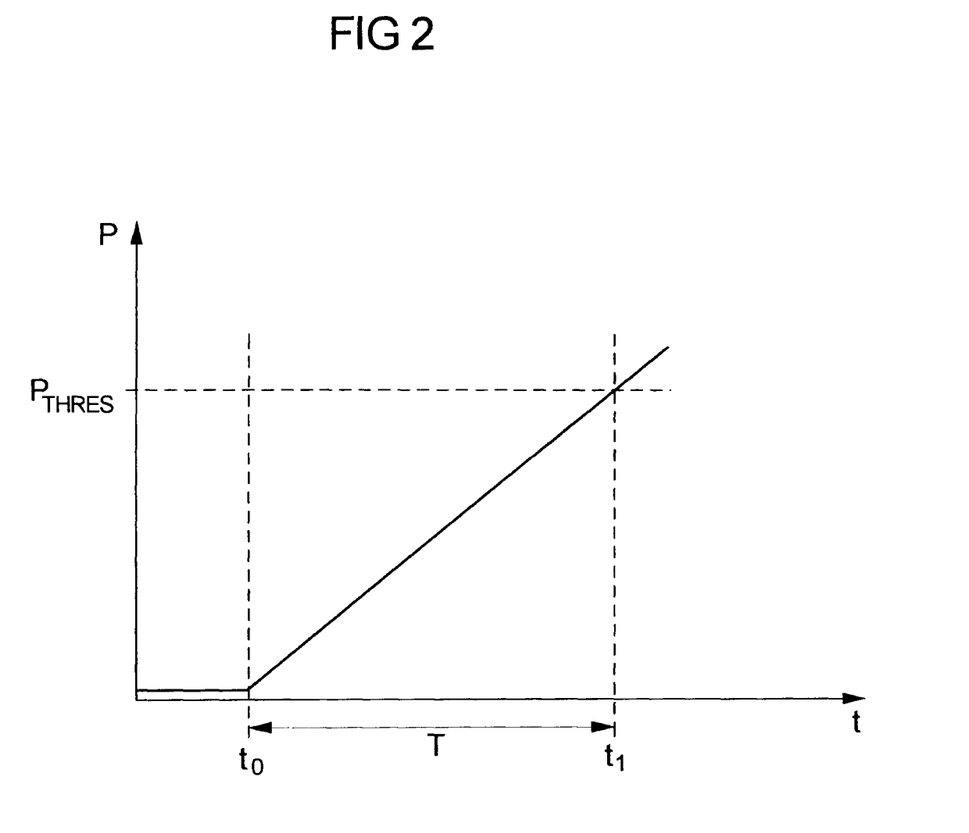
FIG. 2 shows a schematic diagram of a pressure rise over time in case of an occlusion.

FIG. 2 shows in a schematic diagram the pressure P over time t in case of an occlusion O. Generally, the pressure P is very small (almost 0) during normal infusion operation in case no occlusion O is present (see the pressure P prior to the time t0). If at the time t0 an occlusion O occurs, the pressure P will start to rise and will continue to rise (if the occlusion O does not disappear) until a threshold value $P_{thres}$ is exceeded, at which moment an alarm is triggered by the processor device 15 such that a user is warned of the occlusion O.

The occlusion O, in the example of FIG. 2, occurs at time t0. Until the pressure threshold value $P_{thres}$ actually is exceeded by the pressure curve P at time t1, a substantial time duration T may pass, due to the continuous rise of the pressure P following the occlusion O at a finite slope, the slope of the pressure rise herein depending on a multiplicity of factors, for example the flow rate and the compliance of the system, in particular the compliance of the cylindrical tube 20 of the syringe 2 and of the line set 3 extending in between the cylindrical tube 20 and the patient B.

Generally, the pressure in the line set 3 will rise according to the following equation:

$$P = \frac{f \cdot t}{C}.$$

Herein, P denotes the pressure, f denotes the flow rate, t denotes the time, and C denotes the compliance.

Making use of the above equation, a threshold value $P_{thres}$ may be determined—in an initial phase prior to the actual operation for administering a medical solution to a patient B—in order to obtain a fast occlusion detection. Namely, if the compliance C and the flow rate f is known, by assuming a desired time which shall lapse between the actual occurrence of an occlusion and the moment at which the pressure exceeds the pressure threshold value $P_{thres}$ an optimum pressure threshold $P_{thres}$ can be determined, which is low such that a fast occlusion detection may be obtained.

If however the pressure threshold value $P_{thres}$ is chosen too small, false alarms may be triggered, which may hinder the usability of the infusion device 1.

Hence, in one embodiment, within an infusion device 1 the pressure threshold value $P_{thres}$ may be chosen according to two criteria, the first criteria taking into account the desired time and the second criteria serving to limit the likelihood for false alarms.

According to the first criteria, a first pressure threshold value candidate can for example be determined according to the following equation:

$$P_{thres,1}[\text{bar}] = \frac{T_{desired}[h] \cdot f[\text{ml}/h]}{C[\text{ml}/\text{bar}]}.$$

Herein, $P_{thres,1}$ represents the first threshold value candidate in bar, $T_{desired}$ represents the desired time (in hours) between the time t0 of an occurrence of an occlusion O in the line set 3 and the time t1 at which the pressure value exceeds the threshold value $P_{thres}$, C represents the compliance value (in ml/bar), and f represents the flow rate (in ml/h).

The compliance value C associated with the syringe 2 and the line set 3 is stored in the storage device 16 of the infusion device 1. The storage device 16 in this regard may store a multiplicity of compliance values C for different syringes 2 and different line sets 3 such that, by inputting for example the type of syringe 2 to the infusion device 1, the processor device 15 may refer to the compliance value C associated with the particular syringe 2 used on the system for computing the estimate of the duration T.

The storage device 16 may for example store a compliance value for a syringe 2 of a particular manufacturer and a particular volume. The storage device 16 may in addition store a default value for a syringe 2 of a particular volume, which may be used in case a particular syringe 2 of a particular manufacturer is not explicitly defined in the infusion device 1. A line set 3 may be identified by its length, its inner and/or outer diameter or the like and by its manufacturer, and associated with a particular type of line set 3 a particular compliance value may be stored in the storage device 16.

The storage device 16 may store a constant value for the compliance. Just as well it is conceivable that the storage device 6 stores a nonlinear relation for the compliance depending for example on the pressure in the system.

If this first pressure threshold value candidate would be chosen as the pressure threshold value $P_{thres}$, a fast occlusion detection would be obtained. This however may potentially come at the expense of a possibly increased likelihood of a false alarm if the pressure threshold value $P_{thres}$ is chosen too small in this way.

Therefore, a second criteria may—optionally—be applied in addition to determine the threshold value $P_{thres}$.

The second criteria may be derived based on the following background:

To observe the pressure in the line set 3, the force applied to the piston head 210 of the piston 21 by means of the pusher device 11 is measured by the sensor 14 placed in between the pusher device 11 and the piston head 210. The force measured in this way allows for an indirect measurement of the pressure within the cylindrical tube 20, which generally equals the pressure in the line set 3. In particular, the pressure in the cylindrical tube 20 depends on the measured force according to the following relation:

$$P = \frac{F - F_0}{S}.$$

Herein, P denotes the pressure, F denotes the measured force, $F_0$ denotes a frictional force component and S denotes the effective surface by which the piston 21 acts onto the liquid contained in the cylindrical tube 20. The effective surface S is substantially determined by the inner diameter of the cylindrical tube 20.

By determining the pressure P in this way and by comparing the determined pressure P to a predefined threshold $P_{thres}$ it can then be concluded whether an occlusion O is present in the line set 3 or not. In particular, if it is found that the pressure P rises above the threshold $P_{thres}$, it is concluded that an occlusion O is present.

Whereas F is measured and S is known from the geometrical dimensions of the cylindrical tube 20 of the syringe 2, the frictional force component $F_0$ may vary in dependence on the specific syringe 2 used on the system, wherein the frictional force component $F_0$ generally is dependent on the position of the piston 21 within the cylindrical tube 20 and on the velocity by which the piston 21 is moved relative to the cylindrical tube 20 during an infusion process.

The frictional force component $F_0$ may for example depend on the following parameters: the syringe brand, model and batch, the pushing velocity, the position of the piston on its full travel range, the temperature, the waiting time between syringe preparation and infusion start, the liquid inside the syringe, and the pressure. (The catheter size, the extension line diameter and length and the drug viscosity generally can be considered to have no influence on the frictional force. But these parameters may of course have an influence on the pressure.)

In addition, the structural characteristics in particular of the cylindrical tube 20 in which the piston 21 is moved may vary along the travel range of the piston 21 relative to the cylindrical tube 20. In particular, the cylindrical tube 20 may not exhibit a constant diameter, but the diameter may (slightly) change over position, i.e. it may decrease or increase. From such structural variations, a variation of the frictional force over the position may arise.

Hence, for a particular syringe of a particular model, a particular batch, a particular volume and a particular brand a very specific dependence of the frictional force on the position may arise. Generally, the frictional force may be obtained from a statistical analysis by measuring different syringes of different types, models and volumes with respect to their friction as a function of position of the piston 21 relative to the tube 20 and, possibly, also as a function of the velocity by which the piston 21 is moved relative to the tube 20. From such statistical analysis for example a mean frictional force associated with a particular syringe (of a particular type, model, brand and volume) may be stored in the storage device 16. In addition, also the standard deviation of this mean frictional force may be stored for the particular syringe, the standard deviation indicating, as known from statistics, a possible deviation of a true frictional force from the stored mean frictional force.

Generally, if a particular syringe 2 is used and if the true frictional force occurring between the piston 21 and the tube 20 is equal or at least close to the mean frictional force, the pressure value derived from the equation $$P = \frac{F - F_0}{S}.$$

will be (close to) 0 if no occlusion O is present, because it can be assumed that the measured force F is equal (or at least close) to the mean frictional force used as frictional force component F0 in the above equation. If however the true frictional force significantly deviates from the stored mean frictional force and if the stored mean frictional force is used in the above equation, the derived pressure value P deviates from the actual pressure P in the line set 3, which possibly may give rise to false alarms.

The likelihood for false alarms hence depends on the possible deviation of the true frictional force from the frictional force component used in the above equation. If in the above equation the stored mean frictional force (obtained for example from a statistical analysis of a multiplicity of syringes of a particular type, model, volume and brand) is used, the standard deviation expresses a possible deviation of a used syringe from the stored mean frictional force.

Hence, the stored standard deviation for a particular syringe (of a particular type, model, volume and brand) can be used to derive a second criteria, namely a second pressure threshold value candidate. For example, by multiplying the standard deviation by a constant factor, for example a factor of 2, a force error estimate may be derived, which then can be used to calculate the second threshold value candidate according to the following equation:

$$P_{thres,2}[\text{bar}] = \frac{F_{est}[gf]}{10.2 \cdot S[\text{mm}^2]}$$

Herein, $P_{thres,2}$ represents the second threshold value candidate (in bar), $F_{est}$ represents the force error estimate (in gram force (gf)) computed from for example the standard deviation (by multiplying the standard deviation by a constant factor), and S represents the effective cross sectional surface (in mm²) of the tube (20), defined as $S=\pi \cdot (D/2)^2$, D being the inner diameter of the cylindrical tube 20.

There are other possibilities to compute the force error estimate $F_{est}$. For example, the force error estimate may be computed by multiplying the mean frictional force stored in the storage device 16 by a constant factor, for example a factor of 1.5. Or the force error estimate may be stored directly as a parameter for different syringes of different types, models, volumes and brands within the storage device 16.

The actual pressure threshold $P_{thres}$ then is chosen in the infusion device 1 as the maximum of the first threshold value candidate and the second threshold value candidate. In addition, limits may be defined, such that the pressure threshold value may not be lower than a lower limit (for example 50 mmHg) and not be higher than an upper limit (for example 900 mmHg).

By applying the above outlined scheme, the pressure threshold value $P_{thres}$ may be determined by the infusion device 1 in the initial phase prior to the actual operation in an automatic manner. The threshold value $P_{thres}$ hence does not need to be set by a user, but is determined automatically by the infusion device 1 upon initial configuration of the system.

The automatic computing of the threshold value $P_{thres}$ is reliable and works well for the occlusion detection during actual operation in particular in situations in which the infusion device 1 acts on a line set 3 having a single infusion line, hence with no other, external pressure sources (such as other infusion devices) present on the line set 3.

Figure 3:
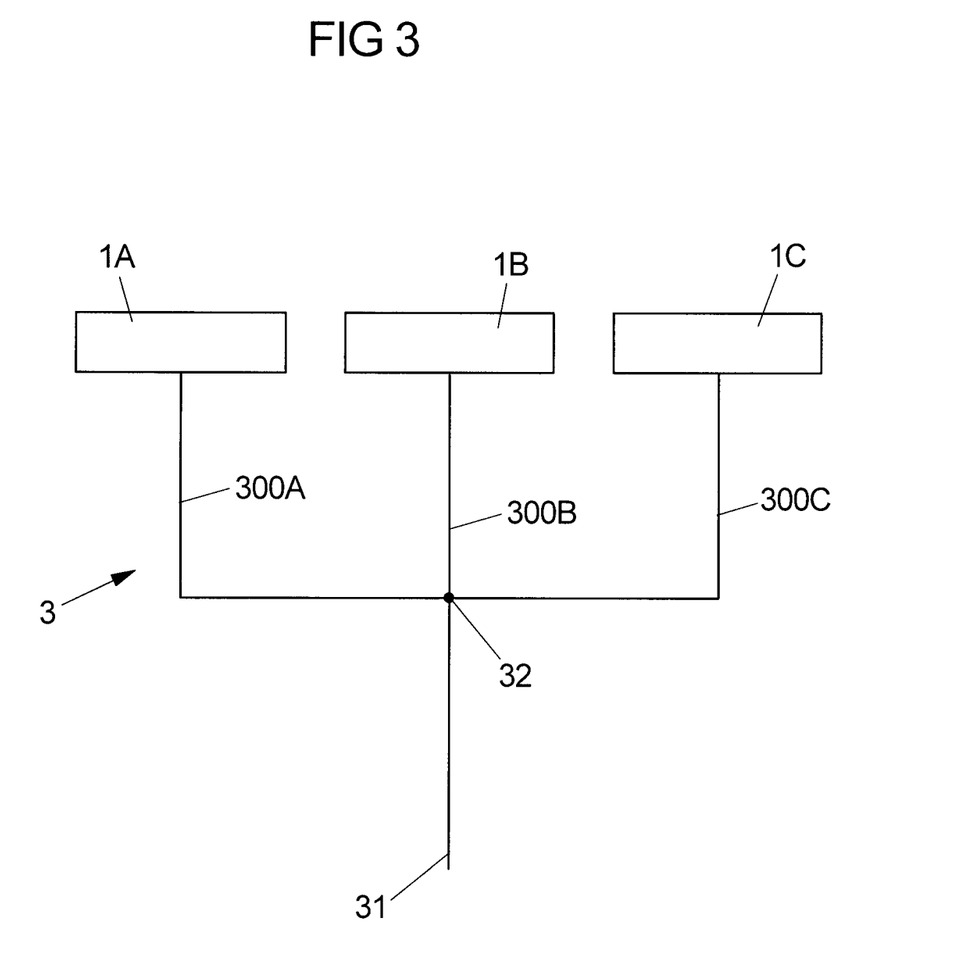
FIG. 3 shows a schematic of a multiline infusion using multiple infusion devices.

However, in multiline infusions such as illustrated in FIG. 3, in which multiple infusion devices 1A, 1B, 1C act on a common line set 3 via infusion lines 300A, 300B, 300C connected to each other at a junction point 32, the pressure within the line set 3 is influenced by all infusion devices 1A, 1B, 1C, such that a pressure variation in the line set 3 does not originate only from a single pressure source, but from the multiple infusion devices 1A, 1B, 1C. This may lead to a situation in which for example a bolus is given by one of the infusion devices 1A, 1B, 1C causing a steep rise of pressure in the line set 3, potentially leading to the observation of a pressure rise at another infusion device 1A, 1B, 1C beyond the threshold value $P_{thres}$ as automatically determined during the initial phase at this other infusion device 1A, 1B, 1C. Such pressure rise hence may lead to the triggering of a false alarm at the other infusion device 1A, 1B, 1C.

In order to differentiate, at an infusion device 1, an occlusion condition from a pressure variation condition in line set 3 other than an occlusion condition, it herein is proposed to monitor the slope of the pressure rise in the line set 3 versus an expected slope, i.e., a slope that can be expected during an occlusion condition. If it is found at an infusion device 1A, 1B, 1C that the slope of the pressure rise in the system substantially deviates from the expected slope, it can be concluded that the pressure rise is not due to an occlusion in the line set 3, but due to another one of the infusion devices 1A, 1B, 1C, for example due to a bolus given by another infusion device 1A, 1B, 1C.

An occlusion will generally cause a rise of the measured force according to a rather well-defined slope, which can be determined when mechanical characteristics of the system such as the compliance of the line set 3, the compliance of the syringe 2 and the stiffness of the mechanical system of the pusher device 11 are known. The expected slope is the theoretical slope that the pressure should follow in case the line is occluded at the catheter level. It depends for example on the flowrate, the syringe mechanical properties (especially the syringe stopper stiffness), the syringe pump mechanical properties (especially the pusher stiffness), the line set mechanical properties (the tube compliance), and the fluid properties (which can be neglected if it is assumed that the fluid to be pumped is an incompressible liquid).

The pressure slope can either be expressed referring to time or referring to volume. Expressing the expected slope with reference to volume, the expected slope at a position i during movement of the piston 21 of the comes out to be:

$$\text{Expected\_slope}(i)[\text{bar/ml}] = \frac{dP(i)[\text{bar}]}{dVolume(i)[\text{ml}]}$$

The expected slope is equivalent to a volumetric stiffness, which is the inverse of the system compliance. One can therefore write $$\frac{1}{\text{Volumetric\_Stiffness}[\text{bar/ml}]} = \sum_{k=1}^{3} \frac{1}{\text{Volumetric\_Stiffness}(k)[\text{bar/ml}]}$$

$$\text{Where} \begin{cases} \text{Volumetric\_Stiffness}(1)[\text{bar/ml}] = \dfrac{1}{\text{Syringe\_Compliance}[\text{ml/bar}]} \\ \text{Volumetric\_Stiffness}(2)[\text{bar/ml}] = \dfrac{1}{\text{Line\_Compliance}[\text{ml/bar}]} \\ \text{Volumetric\_Stiffness}(3)[\text{bar/ml}] = \dfrac{100 \cdot \text{Pusher\_Stiffness}[gf/\text{mm}]}{\text{Syringe\_Surface}[\text{mm}^2]^2} \end{cases}$$

and the expected slope comes out to be:

$$\text{Expected\_slope}[\text{bar/ml}] = \frac{1}{\text{Syringe\_Compliance}[\text{ml/bar}] + \text{Line\_Compliance}[\text{ml/bar}] + \dfrac{\text{Syringe\_Surface}[\text{mm}^2]^2}{100 \cdot \text{Pusher\_Stiffness}[gf/\text{mm}]}}$$

This can be converted to a slope by millimeter, assuming that for a different syringe 1 mm is equivalent to (syringe_Surface S [mm$^2$]/1000) ml:

$$\text{Expected\_slope}[\text{bar/mm}] = \frac{\text{Syringe\_Surface}[\text{mm}^2]}{1000 \cdot \dfrac{(\text{Syringe\_Compliance}[\text{ml/bar}] + \text{Line\_Compliance}[\text{ml/bar}])}{} + 10 \cdot \dfrac{\text{Syringe\_Surface}[\text{mm}^2]^2}{\text{Pusher\_Stiffness}[gf/\text{mm}]}}$$

This also can be converted to gf/mm. Assuming that for a given syringe F[gf]=10.2*P[bar]*S[mm$^2$], the slope in bar/mm can be converted into a slope in gf/mm:

$$\text{Expected\_slope}[gf/\text{mm}] = \frac{0.0102 \cdot \text{Syringe\_Surface}[\text{mm}^2]^2}{(\text{Syringe\_Compliance}[\text{ml/bar}] + \text{Line\_Compliance}[\text{ml/bar}]) + \dfrac{\text{Syringe\_Surface}[\text{mm}^2]^2}{\text{Pusher\_Stiffness}[gf/\text{mm}]}}$$

Example parameter values for a 5 cc syringe of a particular brand and a particular infusion device are summarized in Table 3:

TABLE 3

| Parameter | Value |
| --- | --- |
| syringe_Compliance | 0.0566 ml/bar |
| Line_Compliance | 0.145 ml/bar |
| Pusher_Stiffness | 9279 gf/mm |
| syringe inner diameter | 11.87 mm |
| syringe surface S | 110.66 mm$^2$ |

Using these parameters, the following values for the expected slope are obtained:

Expected_Slope[bar/ml]=4.65[bar/ml]

Expected_Slope[bar/mm]=0.514[bar/mm]

Expected_Slope[gf/mm]=568.8[gf/mm]

This expected slope is independent of the flow rate.

Thus, it can be assumed that, in the above case, the expected slope in case of an occlusion will be close to 0.5 bar/mm for the particular syringe and the particular infusion device for which the parameters are valid.

The expected slope may for example be computed for the particular parameters of the line set 3, the syringe 2 and the device 1 in use upon installation of a particular syringe 2 in connection with a line set 3 on the infusion device 1.

In order to allow the computation of the expected slope, the storage device 16 of the infusion device 1 stores relevant parameters of different syringes 2 and line sets 3 which potentially may be used on the infusion device 1. In the storage device 16 in particular a syringe compliance for one or multiple syringes 2, a line compliance for one or multiple line sets 3, a pusher stiffness of the pusher device 11 (including its driving mechanism), and geometric data of one or multiple syringes 2, in particular an inner diameter of the cylindrical tube 20, may be stored. Hence, upon identification of a particular syringe 2 and a particular line set 3 by a user, for example by inputting suitable control data into the infusion device 1 upon installation of the syringe 2 and the line set 3 on the infusion device 1, the expected slope can be computed and can be used as it shall be described subsequently.

Knowing the expected slope, generally an occlusion condition can be differentiated from other pressure variation conditions, in particular in a multiline infusion scenario. For example, during the operation of an infusion device 1A, 1B, 1C, which may not know that other infusion devices 1A, 1B, 1C are present and are operated to administer medical fluids to a patient B via the same line set 3, the slope of a pressure variation in the line set 3 may be monitored by the infusion device 1A, 1B, 1C and may be compared to the expected slope in order to test whether the threshold value $P_{thresh}$ determined automatically in the initial phase may be assumed reliable and adequate or should be adjusted. If during operation of the infusion device 1A, 1B, 1C it is found that a slope value determined based on measurement values of the sensor device 14 indicative of a pressure variation in the line set 3 deviates by more than a predefined margin from the expected slope, it may be concluded that a pressure variation condition other than an occlusion condition is present in the line set 3, such that it may be determined that the threshold value $P_{thresh}$ may have to be adjusted.

In one embodiment, the processor device 15 of the infusion device 1A, 1B, 1C may be configured to adjust the threshold value $P_{thresh}$ if it is found that the slope value is larger than a predefined first constant α1 times the expected slope value:

slope value>expected slope·α1

The constant α1 herein may have a value in the range between 1 and 10, for example between 2 to 4, in particular 3. If it hence is found that the slope value of the pressure rise as determined from current measurement values of the sensor device 14 is substantially larger than the expected slope, it is concluded that the pressure rise is not due to an occlusion in the line set 3, but to another pressure source external to the infusion device 1A, 1B, 1C. In this case it is concluded that the threshold value $P_{thresh}$ determined automatically in the initial phase is no longer adequate, and consequently the threshold value P thrash is adapted by the processor device 15 of the infusion device 1A, 1B, 1C.

For example, the threshold value $P_{thresh}$ in this case may be set to a maximum default value of the system. Alternatively, the threshold value $P_{thresh}$ may be set to the value of the currently measured pressure plus a predefined margin $\Delta_{pressure}$, equal to for example 50 mmHg.

For the subsequent operation, then, the adjusted threshold value $P_{thresh}$ is used, the adjusted threshold value $P_{thresh}$ being substantially larger than the initially set threshold value $P_{thresh}$. In this way, hence, false alarms may be avoided during abnormal pressure variation conditions.

If during the subsequent operation it is found that the slope of the pressure rise decreases, and if it furthermore is found that the actually measured pressure also decreases, the threshold value $P_{thresh}$ may be reset to the initially set threshold value $P_{thresh}$. For example, if it is found that the slope value falls below the expected slope value times a second predefined constant α2 and furthermore the currently measured pressure in the line set 3 falls below an initially measured pressure (prior to the adjustment of the threshold value $P_{thresh}$), the threshold value $P_{thresh}$ may be reset to the initially set threshold value $P_{thresh}$.

The second predefined constant α2 may have a value in the range between 0.5 and 10. The second predefined constant α2 may have the same value as the first predefined constant α1, or may differ from the first predefined constant α1.

The infusion device 1A, 1B, 1C hence assumes regular operation using the threshold value $P_{thresh}$ which has automatically been determined and set during the initial phase.

Because dependent on the operation and a characteristic of a pressure rise observed during the actual operation the initially set threshold value $P_{thresh}$ is variably adjusted, reliability of an occlusion detection may be improved, in particular by avoiding false alarms in multiline infusion situations. An infusion device 1, 1A, 1B, 1C hence may provide for a reliable, fast occlusion detection as well as a limited amount of false alarms.

The invention is not limited to the embodiments described above, but can be carried out in an entirely different fashion. In particular, the invention generally is applicable to different kinds of infusion devices used for different purposes for administering a medical fluid into a patient.

The expected slope may be determined in a different way, for example in a calibration measurement on a particular syringe and a particular line set. The described procedure hence only serves as an example.

LIST OF REFERENCE NUMERALS

1 Infusion device
10 Housing
100 Front face
11 Pusher device
12 Receptacle
13 Display device
14 Force sensor
15 Processor device
16 Storage device
2 Pumping device (syringe)
20 Cylindrical tube
21 Piston
210 Piston head
3 Line set
30, 31 End
300A, 300B, 300C Line section
32 Junction point
A Actuation direction
B Patient
O Occlusion
P Pressure
$P_{thres}$ Pressure threshold
t time
T Duration

The invention claimed is:

1. An infusion device for administering a medical fluid to a patient, comprising:
a pump mechanism for administering a medical fluid to a patient through a line set,
a sensor for measuring a measurement value indicative of a pressure in the line set, and
a processor configured to automatically set, in an initial phase, a threshold value to a value determined based on at least a mechanical characteristic of at least one of the line set and the pump mechanism and to determine, in an operational phase, whether an occlusion condition in the line set is present based on the measurement value and the threshold value,
wherein the processor is configured to increase the threshold value if in the operational phase a pressure variation condition in the line set different than an occlusion condition is detected by the processor,
wherein, for detecting the pressure variation condition, a slope value indicative of a slope of the pressure in the line set is determined based on measurement values obtained from the sensor, and wherein the processor is configured to conclude that the pressure variation condition different than the occlusion condition is present if the slope value deviates from an expected slope value by more than a predetermined margin.

2. The infusion device according to claim 1, wherein the expected slope value is determined by taking one or more of a compliance of a syringe connected to the line set, a compliance of the line set, a stiffness of the pump mechanism and a dimension of the syringe into account.

3. The infusion device according to claim 2, further comprising a memory configured to store values for one or more of the compliance of at least one syringe, the compliance of at least one line set, the stiffness of the pump mechanism and the dimension of at least one syringe.

4. The infusion device according to claim 1, wherein the processor is configured to conclude that the pressure variation condition different than the occlusion condition is present based on a condition that the slope value is larger than the expected slope value times a first predetermined constant.

5. The infusion device according to claim 1, wherein the processor is configured to set the threshold value to a value larger than the value of the threshold value set during the initial phase if the pressure variation condition different than the occlusion condition is detected.

6. The infusion device according to claim 1, wherein the processor is configured to reset the threshold value to the value of the threshold value set during the initial phase based on a condition that the slope value falls below the expected slope value times a second predetermined constant.

7. The infusion device according to claim 1, wherein the processor is configured, for determining the value of the threshold value during the initial phase, to determine a first threshold value candidate based on a desired time between a time of an occurrence of an occlusion in the line set and a time of the determining of the occlusion condition by the processor.

8. The infusion device according to claim 7, wherein the processor is configured to compute the first threshold value candidate using a stored compliance value, a set flow rate and the desired time.

9. The infusion device according to claim 8, wherein the processor is configured to compute the first threshold value candidate using the following equation:

$$P_{thresh,1}[\text{bar}] = \frac{T_{desired}[\text{h}] \cdot f[\text{ml/h}]}{C[\text{ml/bar}]}$$

wherein
$P_{thres,1}$ represents the first threshold value candidate (in bar),
$T_{desired}$ represents the desired time (in hours),
C represents the stored compliance value (in ml/bar), and
f represents the set flow rate (in ml/h).

10. The infusion device according to claim 8, further comprising a memory configured to store a multiplicity of compliance values associated with a multiplicity of at least one of different syringes and different line sets.

11. The infusion device according to claim 7, wherein the infusion device is a syringe pump comprising a receptacle for receiving a syringe having a tube containing a medical fluid and a piston movable with respect to the tube, and a pusher device for acting onto the piston for pumping the medical fluid from the tube towards a patient, wherein the processor is configured, for determining the value of the threshold value during the initial phase, to determine a second threshold value candidate computed based on a force error estimate of a possible deviation between an expected frictional force and a true frictional force occurring when moving the piston relative to the tube.

12. The infusion device according to claim 11, wherein the second threshold value candidate is computed according to the following equation:

$$P_{thresh,2}[\text{bar}] = \frac{F_{est}[gf]}{10.2 \cdot S[\text{mm}^2]}$$

wherein $P_{thres,2}$ represents the second threshold value candidate (in bar), $F_{est}$ represents the force error estimate (in gram force (gf)), and S represents the effective cross sectional surface (in mm$^2$) of the tube, defined as S=π·(D/2)$^2$, D being an inner diameter of the cylindrical tube.

13. The infusion device according to claim 11, wherein the threshold value during the initial phase is set to be a maximum of the first threshold value candidate and the second threshold value candidate.

14. A method for controlling an infusion device for administering a medical fluid to a patient, comprising:

in an initial phase automatically setting, using a processor of the infusion device, a threshold value to a value determined based on at least a mechanical characteristic of at least one of a line set and a pump mechanism for administering a medical fluid to a patient through the line set, and in an operational phase determining, using the processor, whether an occlusion condition in the line set is present based on a measurement value indicative of a pressure in the line set and the threshold value, and increasing the threshold value if in the operational phase a pressure variation condition in the line set different than an occlusion condition is detected by the processor, wherein, for detecting the pressure variation condition, a slope value indicative of a slope of the pressure in the line set is determined based on measurement values obtained from a sensor, and wherein the processor is configured to conclude that the pressure variation condition different than the occlusion condition is present if the slope value deviates from an expected slope value by more than a predetermined margin.

15. An infusion device for administering a medical fluid to a patient, comprising:

a pump mechanism for administering a medical fluid to a patient through a line set, a sensor for measuring a measurement value indicative of a pressure in the line set, and a processor configured to automatically set, in an initial phase, a threshold value to a value determined based on at least a mechanical characteristic of at least one of the line set and the pump mechanism and to determine, in an operational phase, whether an occlusion condition in the line set is present based on the measurement value and the threshold value, wherein the processor is configured to increase the threshold value if in the operational phase a pressure variation condition in the line set different than an occlusion condition is detected by the processor based on a comparison of the pressure variation condition and the occlusion condition, wherein the processor is configured, for determining the value of the threshold value during the initial phase, to determine a first threshold value candidate based on a desired time between a time of an occurrence of an occlusion in the line set and a time of the determining of the occlusion condition by the processor.

16. The infusion device according to claim 15, wherein the processor is configured to compute the first threshold value candidate using a stored compliance value, a set flow rate and the desired time.

17. The infusion device according to claim 16, wherein the processor is configured to compute the first threshold value candidate using the following equation:

$$P_{thresh,1}[\text{bar}] = \frac{T_{desired}[\text{h}] \cdot f[\text{ml/h}]}{C[\text{ml/bar}]}$$

wherein $P_{thres,1}$ represents the first threshold value candidate (in bar), $T_{desired}$ represents the desired time (in hours), C represents the stored compliance value (in ml/bar), and f represents the set flow rate (in ml/h).

18. The infusion device according to claim 16, further comprising a memory configured to store a multiplicity of compliance values associated with a multiplicity of at least one of different syringes and different line sets.

19. The infusion device according to claim 15, wherein the infusion device is a syringe pump comprising a receptacle for receiving a syringe having a tube containing a medical fluid and a piston movable with respect to the tube, and a pusher device for acting onto the piston for pumping the medical fluid from the tube towards a patient, wherein the processor is configured, for determining the value of the threshold value during the initial phase, to determine a second threshold value candidate computed based on a force error estimate of a possible deviation between an expected frictional force and a true frictional force occurring when moving the piston relative to the tube.

20. The infusion device according to claim 19, wherein the second threshold value candidate is computed according to the following equation:

$$P_{thresh,2}[\text{bar}] = \frac{F_{est}[gf]}{10.2 \cdot S[\text{mm}^2]}$$

wherein $P_{thres,2}$ represents the second threshold value candidate (in bar), $F_{est}$ represents the force error estimate (in gram force (gf)), and S represents the effective cross sectional surface (in mm$^2$) of the tube, defined as S=π·(D/2)$^2$, D being an inner diameter of the cylindrical tube, and the threshold value, during the initial phase is set to be a maximum of the first threshold value candidate and the second threshold value candidate.

* * * * *